United States Patent [19]
McCowan et al.

[11] Patent Number: 5,314,413
[45] Date of Patent: May 24, 1994

[54] SAFETY VIAL-HANDLER TOOL AND METHOD

[76] Inventors: Deborah McCowan, 2712 Courtland Blvd., Deltona, Fla. 32738; Diana McCoy, 524 Gaspar Ave., Deltona, Fla. 32725

[21] Appl. No.: 121,542

[22] Filed: Sep. 16, 1993

[51] Int. Cl.⁵ .............................................. A61M 5/32
[52] U.S. Cl. ................................... 604/192; 211/78; 604/263
[58] Field of Search .................. 604/187, 192, 263; 211/77, 78

[56] References Cited
U.S. PATENT DOCUMENTS

| | | | |
|---|---|---|---|
| 4,775,055 | 10/1988 | Morse | 211/78 |
| 4,840,618 | 6/1989 | Marvel | 604/187 |
| 4,921,489 | 5/1990 | Frizzell | 604/263 |
| 4,944,730 | 7/1990 | Plucinski | 604/187 |
| 4,982,850 | 1/1991 | Marvel | 604/187 |
| 4,995,871 | 2/1991 | Sasaki et al. | 604/192 |
| 5,061,248 | 10/1991 | Sacco | 604/192 |
| 5,129,886 | 7/1992 | Sincock | 604/192 |
| 5,156,426 | 10/1992 | Graves | 604/192 |
| 5,160,324 | 11/1992 | Halbach | 604/192 |
| 5,201,717 | 4/1993 | Wyatt et al. | 604/196 |

Primary Examiner—Paul J. Hirsch
Attorney, Agent, or Firm—Edward M. Livingston

[57] ABSTRACT

A safety vial-handler tool has a plurality of different sizes of vial orifices (4) in a vial plate (1) superimposed rotatably on a shield plate (2). The shield plate (2) has a shield orifice (6) sized to receive the largest-diameter vial that is positional in the vial plate (1). A handle (3) is attached perpendicularly to a bottom edge of the shield plate (2). The vial plate (1) is dialed rotatably to align a particular vial-plate orifice with the shield orifice (6) for a vial (7) being handled. A vial that fits a particular vial-plate orifice is then inserted into the vial-plate orifice where it is suspended from a vial flange (8). The vial (7) is extended through the shield plate (2) in parallel relationship to the handle (3). The suspending vial is held with a thumb (9) and forefinger (10) while the handle (3) is grasped with at least one of the remaining three fingers (12) and palm (13) of a hand (11) of a user. The user's other hand is thus free to operate a syringe for transferring a fluid into or out of the vial being so held. A deflector ridge (15, 17) around either the vial plate (1) or the shield plate (2) further restrains syringe needles from sticking the handler. The handle can have an indentation (19, 22) for one or more of the three handle-holding fingers and can be foldable for fitting this vile-handler tool into a pocket of a user's uniform or into a phlebotomist's kit.

21 Claims, 4 Drawing Sheets

SAFETY VIAL-HANDLER TOOL AND METHOD

BACKGROUND OF THE INVENTION

This invention relates to hand-held vial and test-tube holders. In particular, it is a vial-handler tool with a shield for protection against accidentally sticking oneself by a syringe needle when transferring blood or other fluid into or out of a vial of a size for which the tool is dialed for selection from a plurality of vial sizes. A use method is described.

Various vial holders with shields have been devised for protection against contraction of primarily lethal AIDS and also against other infections when transferring contaminated blood or other fluid into or out of a vial with a syringe in the health-care field. None, however, has been foldable for phlebotomy-kit or uniform-pocket carriage; nor have they combined convenient smallness with adaptation to different sizes of vials or test tubes as provided by this invention.

One example of a different device for holding a vial in relation to use with a syringe is described in U.S. Pat. No. 4,840,618 that was issued to Ray D. Marvel on Jun. 20, 1989. The Marvel patent described a hollow handle into which a "test container," such as a vial, was fittable snugly. A protective shield extended over a user's hand radially from the upper end of the handle. It was limited to one size of test container for which a particular unit was sized and shaped precisely. It was not adaptable to different sizes of vials or test containers. Nor was it foldable to fit into a pocket of a uniform or other clothing of a user.

Another holder with a safety shield was taught by U.S. Pat. No. 4,982,850 issued to Donald B. Mears on Jan. 8, 1991. Mears taught a plurality of tubular test-tube holders arranged in a row between a top shield and a bottom base. A frontal slot in each holder allowed application of thumb pressure against test tubes to hold them steadily against movement of a syringe-needle when transferring fluid into or out from one of the test tubes. This device also was not a pocket tool. Instead, it was a container of a plurality of test tubes or vials.

Other known vial holders are further yet different from this invention and do not have the convenience and safety features provided by this invention.

SUMMARY OF THE INVENTION

One object of this invention is to provide a safety vial-handler tool which protects a user against accidentally sticking oneself with a syringe needle when transferring a contaminated fluid into or out of a vial with a syringe.

Another object is to provide a safety vial-handler tool holder that can be uniform-pocket-carried, purse-carried or carried in a phlebotomy kit for convenient use where and as needed.

Another object is to provide a safety vial-handler tool that is independent of multiple-vial containers, such that its use is not hazardous in relation to other vials in a container.

Yet another object is to provide a safety vial-handler tool that is adaptable to holding different sizes of vials or test tubes when transferring a fluid into or out from one of them.

The invention accomplishes the above and other objects with a safety vial-handler tool having a multiple-orifice vial plate superimposed rotatably on a shield plate. The shield plate has a shield orifice sized to receive the largest-diameter vial that is positional in the multiple-orifice vial plate. A handle is attached perpendicularly to a bottom edge of the shield plate. The vial plate may be dialed rotatably to align a particular vial-plate orifice with the shield orifice for a vial being handled. A vial that fits the particular vial-plate orifice is then inserted into the vial-plate orifice where it is suspended from a vial flange. The vial is extended through the shield plate in parallel relationship to the handle. The suspending vial is held with a thumb and forefinger while the handle is grasped with the remaining three fingers and palm of a hand of a user. The user's other hand is used to operate a syringe for transferring a fluid into or out from the vial being so held. A ridge around either the vial plate or the shield plate further restrains syringe needles. The handle can have a groove for the three handle-holding fingers and can be foldable for fitting this vile-handler tool into a pocket of a user's uniform or into a phlebotomist's kit.

BRIEF DESCRIPTION OF THE DRAWINGS

This invention is described by appended claims in relation to description of a preferred embodiment with reference to the following drawings wherein:

DESCRIPTION OF PREFERRED EMBODIMENT

Figure 1:
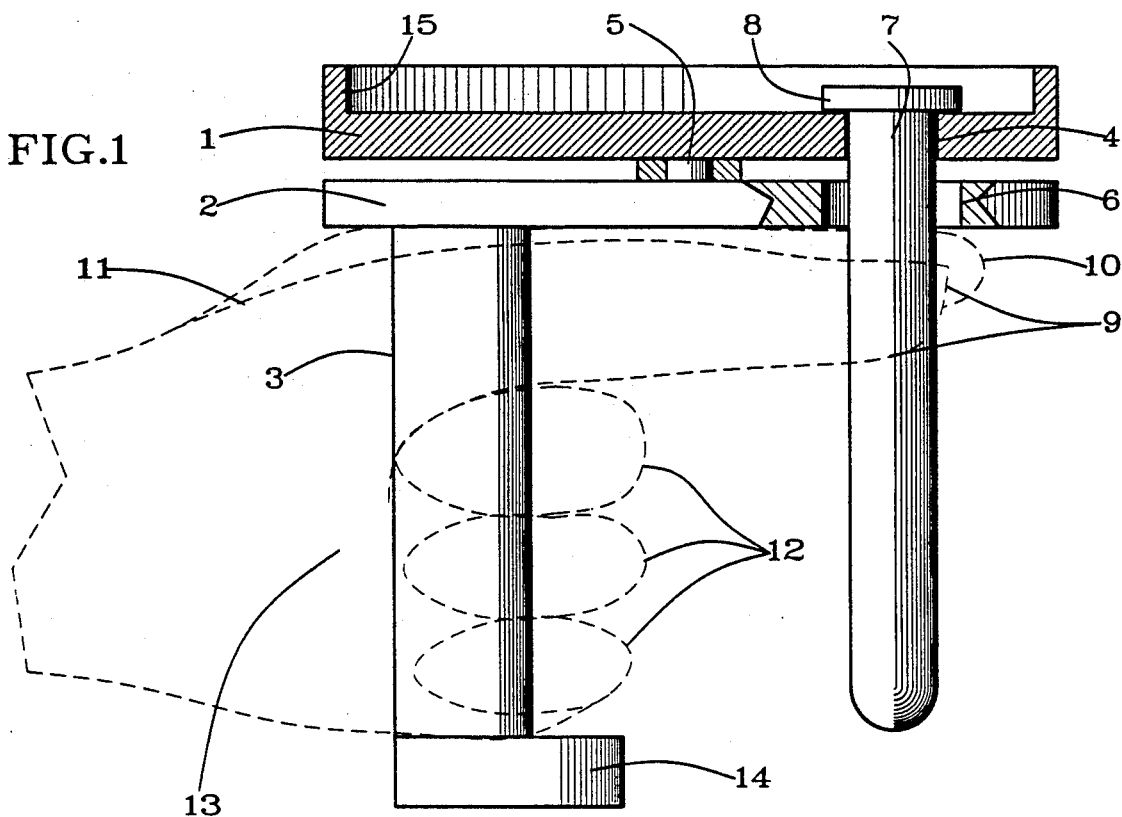
FIG. 1 is a cutaway side view of a fixed-handle embodiment being held by a hand, shown in broken lines, which also holds an inserted vial.
Figure 2:
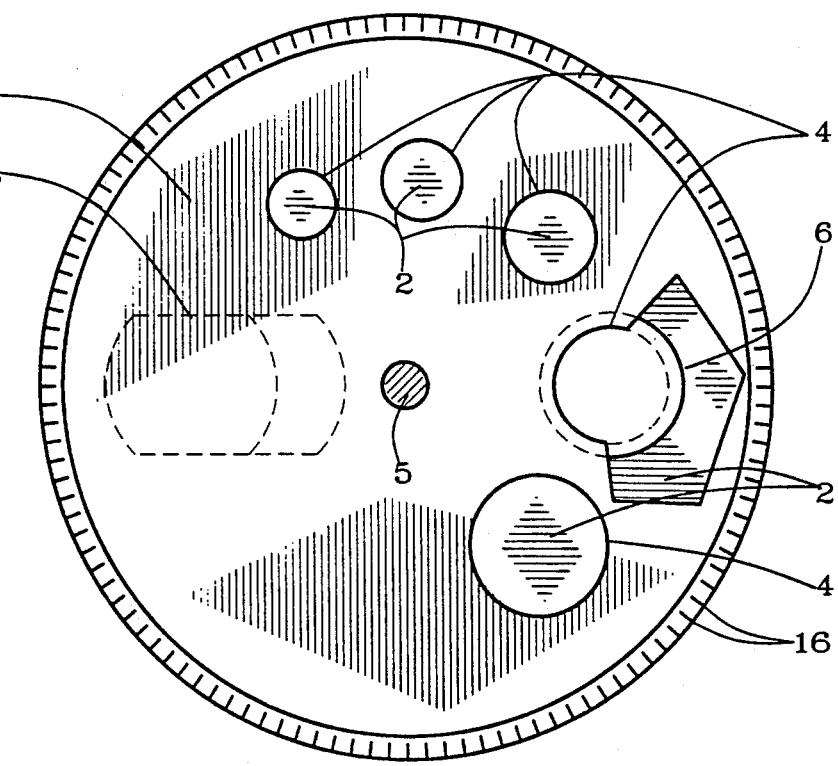
FIG. 2 is a cutaway top view of the FIG. 1 embodiment without a vial inserted.

Reference is made first to FIGS. 1 and 2. A vial plate 1 is rotatable on a shield plate 2 from which a handle 3 is extended perpendicularly downward. A plurality of vial orifices 4 having graduated diameters are positioned at an equal distance from a vial-plate axis 5. A shield orifice 6 having a diameter equal to or greater than the diameter of the largest vial orifice 4 is positioned in the shield plate 2 opposite the handle 3 at the same distance from the vial-plate axis 5 as the vial orifices 4. A vial 7 is positional in a vial orifice 4 selected for a diameter which allows the vial 7 to be inserted into the vial orifice 4 and through the shield orifice 6 to be suspending from a vial flange 8 that rests on the vial plate 1 at an external periphery of the vial orifice 4. The vial plate 1 is dialed rotationally to a circumferential position of alignment of a selected vial orifice 4 and the shield orifice 6.

An inserted vial 7 is held between a thumb 9 and a forefinger 10 of a user's hand 11 while the handle 3 is held between the remaining three fingers 12 and the palm 13 of the user's hand 11. A lateral extension of a base 14 of the handle 3 can be buttressed against a bottom portion of the hand 11 to arrest upward travel of the handle 3 when a syringe needle is removed through tight orifices of a vial lid while a bottom of the shield plate 2 can be buttressed against a top portion of the user's hand 11 to arrest downward travel of the handle 3 when a syringe needle is inserted through a vial lid. A deflector ridge 15 can be positioned at an exterior edge of the vial plate 1 to deflect syringe needles that may slip off of the edge of the vial plate 1 when the vial may be missed by a user due to fatigue, being bumped by another individual or any other reason. The deflector ridge 15 can be used also as a handle for rotating the vial plate 2 and can be provided with knurled serrations 16 for gripping the deflector ridge 15. Usually, however, rotational dialing of the vial plate 1 for alignment of a desired vial orifice 4 with the shield orifice 6 will be accomplished by inserting a finger in a vial orifice 4 for a rotational handle.

The purpose of this safety vial-handler tool is to hold vials 7 only while fluid is being put into or taken from them. It is not intended to be a container, although temporarily, that is its function. Vials are removed from containers for handling with this tool when fluid is being put into or taken from them and then put back into containers afterwards.

Size and proportions of components can vary as desired. The vial plate 1 and shield plate 2 can have smaller diameters in proportion to the handle orifices to make a small unit. Radial position of the vial orifices can be decreased also for a smaller unit that can be carried easily in a pocket of a uniform worn by healthcare personnel such as a phlebotomist, a nurse or a laboratory technician. Distance of separation of the vial plate 1 and the shield plate 2 also can be diminished or eliminated for compactness.

Figure 3:
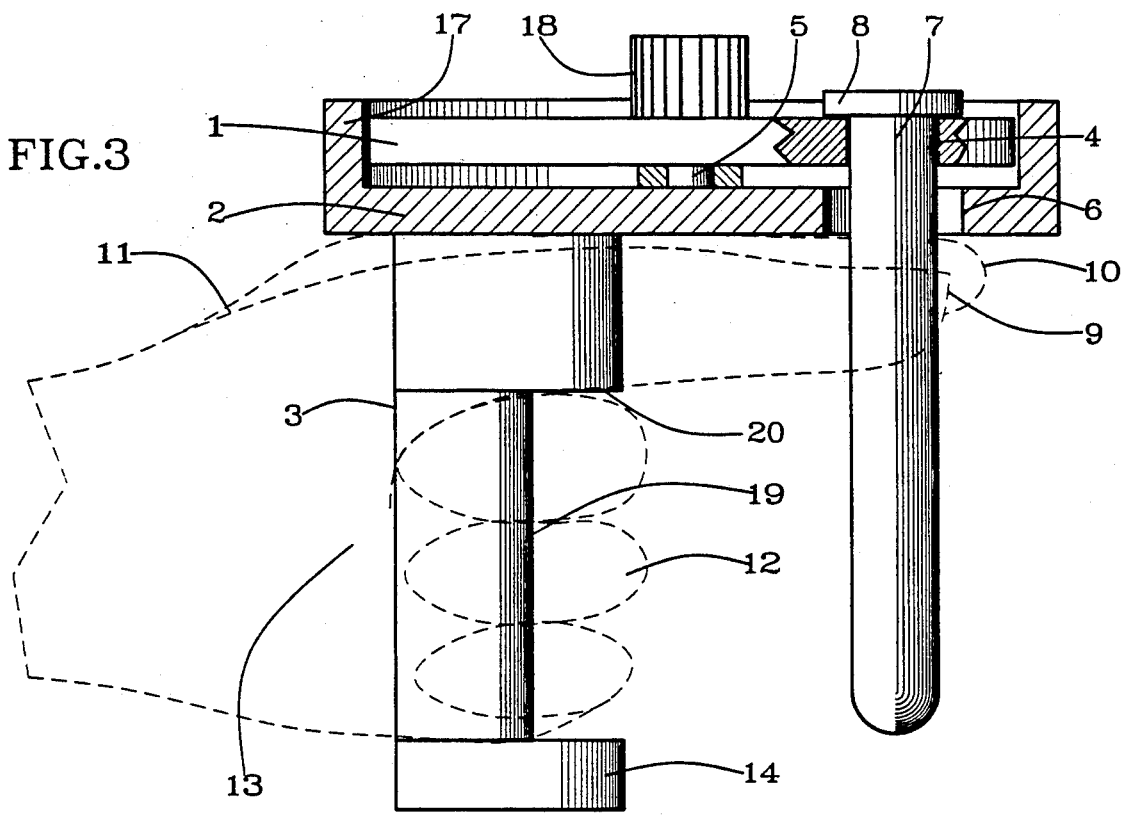
FIG. 3 is a cutaway side view of an embodiment having a deflector ridge on a shield plate, an index knob and a handle with a three-finger indentation.
Figure 4:
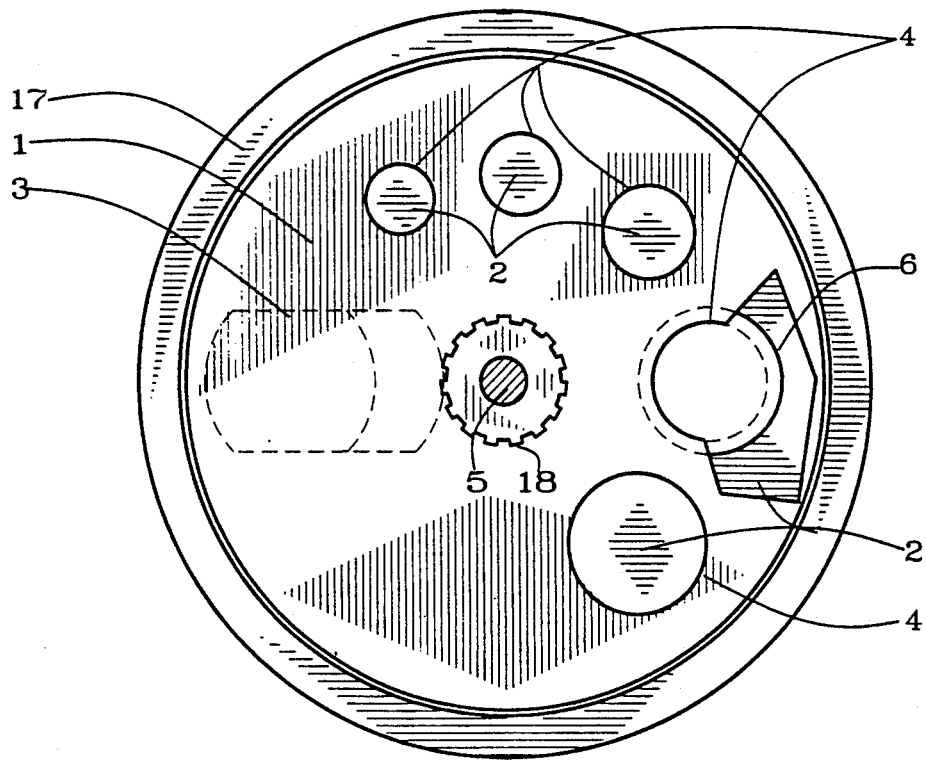
FIG. 4 is a cutaway top view of the FIG. 3 illustration without a vial inserted.

Referring to FIGS. 3 and 4, a shield-plate deflector ridge 17 can be provided as an option to the deflector ridge 15 on the vial plate 1. A dial knob 18 can be added, particularly for units without the deflector ridge 15 if desired for ease in rotating the vial plate 1. The handle 3 can have one or up to three finger indentations 19, one for each remaining finger 12, between the lateral extension of the handle base 14 and a top handle ridge 20. A three-finger indentation 19 as illustrated may be preferable for some users.

Figure 5:
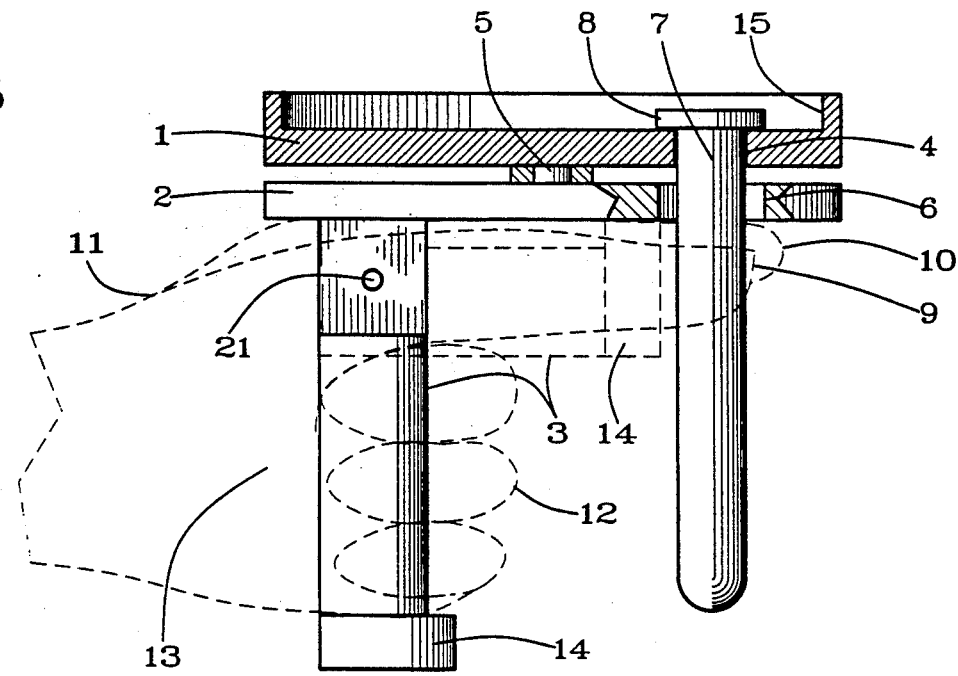
FIG. 5 is a cutaway side view of a small-sized unit having a deflector ridge on a vial plate and a foldable handle being held while also holding an inserted vial.

Referring to FIG. 5, the handle 3 can be foldable on a handle pivot axle 21. A folded mode of the handle 3 is illustrated in broken lines. A smaller unit for smaller hands of users is illustrated also by FIG. 5.

Figure 6:
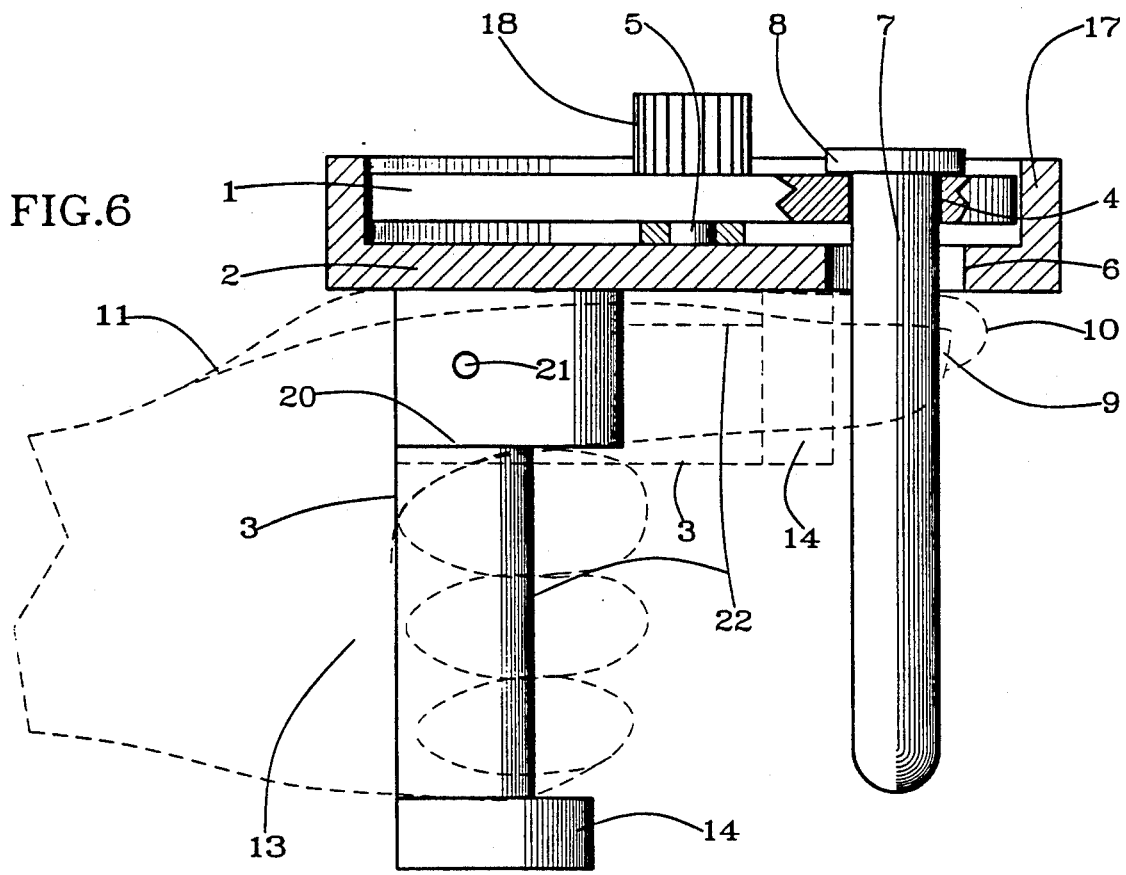
FIG. 6 is a cutaway side view of an embodiment having a deflector ridge on the shield plate and a foldable handle with a three-finger indentation.

Referring to FIG. 6, a handle 3 with a foldable finger indentation 22 can be attached to the handle pivot axle 21 positioned in a top handle ridge 20. This type of handle 3 or any form of handle 3 can be used with either form of vial plate 1 and shield plate 2.

Figure 7:
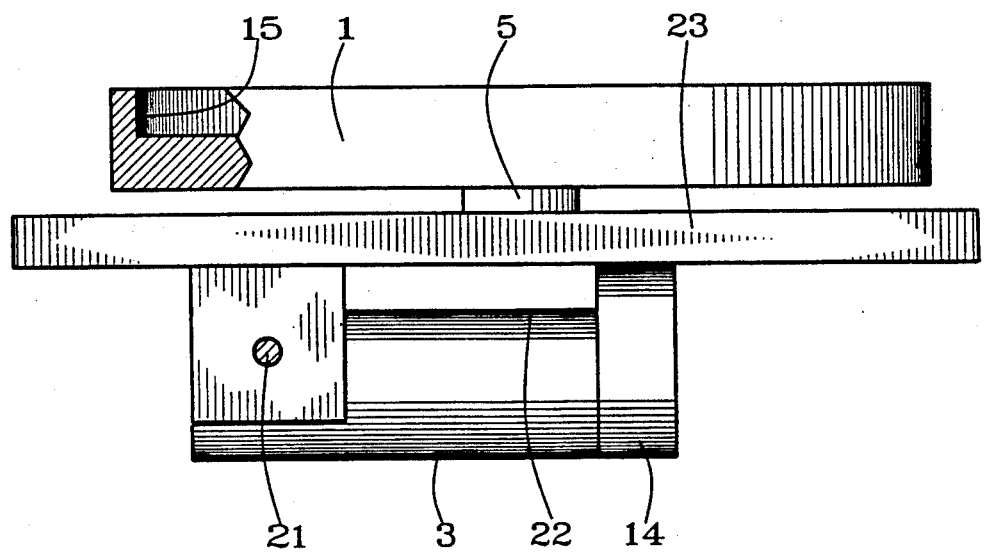
FIG. 7 is a cutaway side view of an embodiment having a rectangular shield plate and a foldable handle in folded mode.
Figure 8:
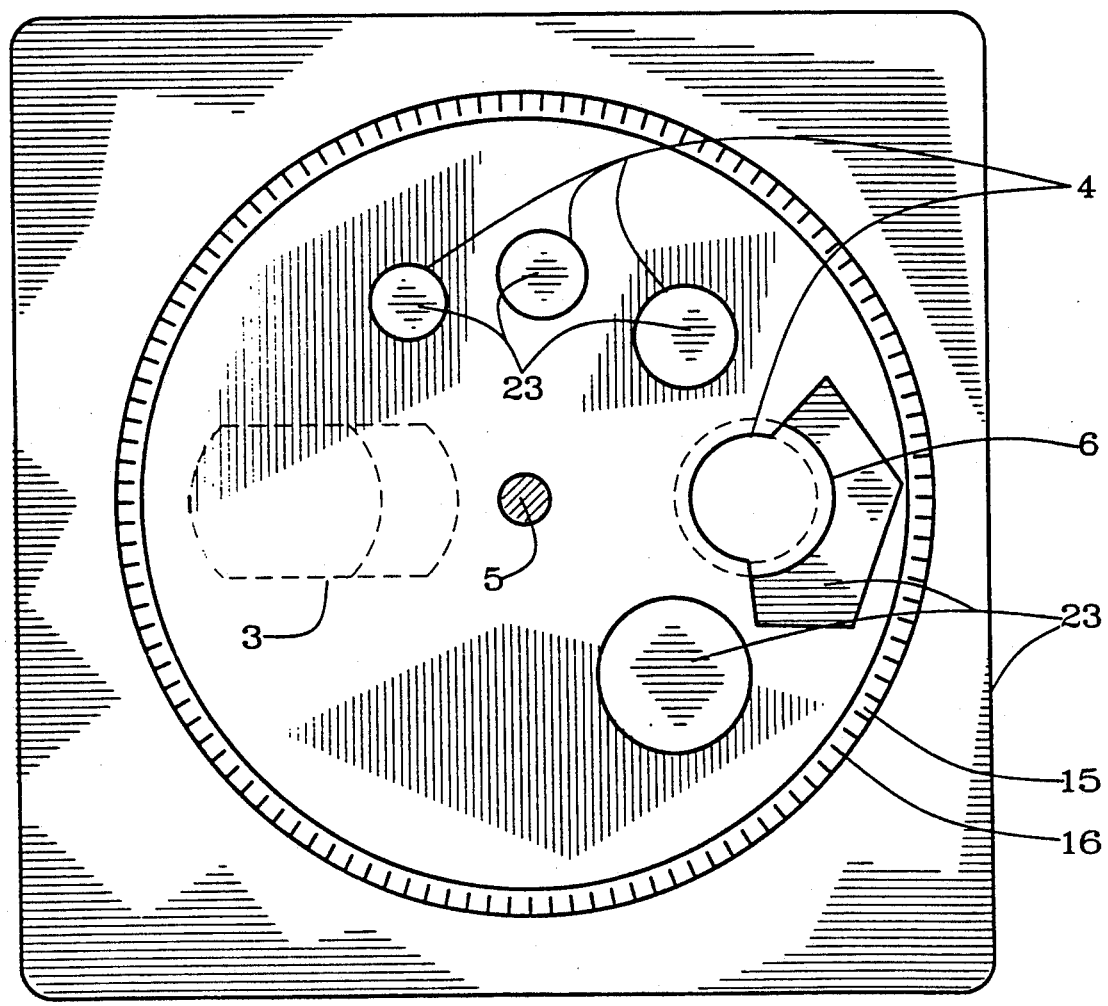
FIG. 8 is a cutaway top view of the FIG. 7 embodiment.

Referring to FIGS. 7 and 8, a rectangular shield plate 23 is optional to a circular shield plate 2 illustrated in FIGS. 1-6. The vial plate 1 also can be different shapes than round if desired. A handle 3 pivotal on a handle pivot axle 21 is shown in folded mode in FIG. 7.

Key factors in design of this tool are to position the handle 3 and the axis of the shield orifice 6 so close together that there is no excess distance between the handle 3 and a vial 7 in aligned orifices 4 and 6 for inserting the three fingers 12 that grasp the handle 3. Radial distance beyond axes of orifices 4 and 6 and height of deflector ridges 15 and 17 should be no more than necessary to deflect needles reliably. This minimizes size of the tool and maximizes its convenience.

A new and useful safety vial-handler tool having been described, all such modifications, adaptations, substitutions of equivalents, combinations of components, applications and forms thereof as described by the following claims are included in this invention.

I claim:

1. A safety vial-handler tool comprising:
   a vial plate superimposed rotatably on a shield plate;
   a plurality of vial orifices in the vial plate positioned at a common radius from a rotational axis of the vial plate;
   each vial orifice having a different diameter sized to contain a vial with a desired diameter;
   a shield orifice in the shield plate positioned at a radial distance from the rotational axis of the vial plate that is equal to the common radius of the plurality of vial orifices from the rotational axis of the vial plate on the shield plate;
   the shield orifice being sized to receive a vial having the largest diameter that is fittable into a vial orifice having the largest desired diameter; and
   a handle extended perpendicularly from a bottom surface of the shield plate, such that the handle is parallel to a vial suspended from a vial orifice and passing through the shield orifice.

2. A safety vial-handler tool according to claim 1 and further comprising:
   a dial handle positioned on a top surface of the vial plate.

3. A safety vial-handler tool according to claim 1 wherein the vial plate is round.

4. A safety vial-handler tool according to claim 3 and further comprising:
   a deflector ridge on a circumferential periphery of the vial plate.

5. A safety vial-handler tool according to claim 4 wherein the shield plate is round.

6. A safety vial-handler tool according to claim 4 wherein the shield plate is rectangular.

7. A safety vial-handler tool according to claim 1 wherein the handle is attached pivotally to a bottom surface of the shield plate such that the handle is foldable from a perpendicular attitude to a horizontal attitude.

8. A safety vial-handler tool according to claim 7 and further comprising:
   at least one finger indentation vertically below a thumb-and-forefinger portion of the handle, such that at least one finger of a user can be used to grasp the handle between a top ridge and a bottom ridge of the at-least-one finger indentation and to arrest respectively upward or downward movement of the handle from insertion of a syringe needle into and removal of a syringe needle from a vial that is positioned in a selected vial orifice and extended through the shield orifice while a forefinger and thumb of the user are used to grasp the said vial.

9. A safety vial-handler tool according to claim 1 and further comprising:
   at least one finger indentation vertically below a thumb-and-forefinger portion of the handle, such that at least one finger of a user can be used to grasp the handle between a top ridge and a bottom ridge of the at-least-one finger indentation and to arrest respectively upward or downward movement of the handle from weight of the safety vial-handler tool and from insertion of a syringe needle into and removal of a syringe needle from a vial that is positioned in a selected vial orifice and extended through the shield orifice while a forefinger and thumb of the user are used to grasp the said vial.

10. A safety vial-handler tool according to claim 1 and further comprising:

a lateral extension of a base of the handle, such that a bottom portion of a user's hand grasping the handle can be buttressed against the lateral extension of the base of the handle to arrest upward travel of the handle when a syringe needle is being removed from a vial that is positioned in a selected vial orifice and extended through the shield orifice and a top portion of the users hand can be buttressed against a bottom surface of the shield plate to support weight of the safety vial-handler tool and to arrest downward travel of the handle when a syringe needle is being inserted into the said vial.

11. A safety vial-handler tool according to claim 10 wherein the handle is attached pivotally to a bottom surface of the shield plate such that the handle is foldable from a perpendicular attitude to a horizontal attitude.

12. A safety vial-handler tool according to claim 1 wherein the vial plate is transparent.

13. A safety vial-handler tool according to claim 1 wherein the shield plate is transparent.

14. A safety vial-handler tool according to claim 13 wherein the vial plate is transparent.

15. A safety vial-handler tool according to claim 1 wherein diameter of the plurality of vial orifices is graduated successively from one to another circumferentially.

16. A safety vial-handler tool according to claim 1 wherein the vial plate and the shield plate are round and further comprising:

a deflector-ridge dial handle extended upwardly from an outside circumferential periphery of the vial plate, such that the deflector-ridge dial handle can be employed to deflect syringe needles and to rotationally dial the vial plate to a circumferential position of alignment of a selected vial orifice with the shield orifice for insertion of a vial into the aligned vial orifice and shield orifice.

17. A safety vial-handler tool according to claim 16 wherein the handle is attached pivotally to a bottom surface of the shield plate such that the handle is foldable from a perpendicular attitude to a horizontal attitude.

18. A safety vial-handler tool according to claim 17 and further comprising:

at least one finger indentation vertically below a thumb-and-forefinger portion of the handle, such that at least one finger of a user can be used to grasp the handle between a top ridge and a bottom ridge of the at-least-one finger indentation and to arrest respectively upward or downward movement of the handle from insertion of a syringe needle into and removal of a syringe needle from a vial that is positioned in a selected vial orifice and extended through the shield orifice while a forefinger and thumb of the user are used to grasp the said vial.

19. A safety vial-handler tool according to claim 17 and further comprising:

a lateral extension of a base of the handle, such that a bottom portion of a user's hand grasping the handle can be buttressed against the lateral extension of the base of the handle to arrest upward travel of the handle when a syringe needle is being removed from a vial that is positioned in a selected vial orifice and extended through the shield orifice and a top portion of the users hand can be buttressed against a bottom surface of the shield plate to support weight of the safety vial-handler tool and to arrest downward travel of the handle when a syringe needle is being inserted into the said vial.

20. A safety vial-handler tool according to claim 16 wherein the vial plate and the shield plate are transparent.

21. A method for using a safety vial-handler tool having:

a vial plate superimposed rotatably on a shield plate;

a plurality of vial orifices in the vial plate positioned at a common radius from a rotational axis of the vial plate;

each vial orifice having a different diameter sized to contain a vial with a desired diameter;

a shield orifice in the shield plate positioned at a radial distance from the rotational axis of the vial plate that is equal to the common radius of the plurality of vial orifices from the rotational axis of the vial plate on the shield plate;

the shield orifice being sized to receive a vial having the largest diameter that is fittable into a vial orifice having the largest desired diameter; and a handle extended perpendicularly from a bottom surface of the shield plate, such that the handle is parallel to a vial suspended from a vial orifice and passing through the shield orifice;

the method comprising the following steps:

(A) grasping the handle with one hand;

(B) rotationally dialing the vial plate to a circumferential position of axial alignment of a selected vial orifice with the shield orifice;

(C) inserting a vial of a selected size into the aligned vial orifice and shield orifice;

(D) grasping the inserted vial with a thumb and forefinger of the hand that is grasping the handle while at least one other finger of the hand grasping the handle and a palm of said hand are employed to grasp the handle; and (E) inserting and removing a needle of a syringe held by an opposite hand of the user respectively into and out from the vial being so grasped.

* * * * *